(12) United States Patent
Korhonen

(10) Patent No.: US 7,258,484 B2
(45) Date of Patent: Aug. 21, 2007

(54) PROTECTIVE GARMENT

(75) Inventor: Eerika Korhonen, Huuvari (FI)

(73) Assignee: PaloDEx Group Oy, Tuusula (FI)

( * ) Notice: Subject to any disclaimer, the term of this patent is extended or adjusted under 35 U.S.C. 154(b) by 62 days.

(21) Appl. No.: 11/304,073

(22) Filed: Dec. 15, 2005

(65) Prior Publication Data

US 2007/0140434 A1 Jun. 21, 2007

(51) Int. Cl.
*A61B 6/14* (2006.01)
(52) U.S. Cl. ...................... 378/191; 378/203; 378/210; 250/516.1
(58) Field of Classification Search ................ 378/191, 378/203, 204, 210; 250/515.1, 516.1; 128/846, 128/849, 854
See application file for complete search history.

(56) References Cited

U.S. PATENT DOCUMENTS

| | | | | |
|---|---|---|---|---|
| 3,052,799 A | * | 9/1962 | Hollands | ................. 250/516.1 |
| 3,233,248 A | * | 2/1966 | Bushnell | ......................... 2/457 |
| 3,569,713 A | * | 3/1971 | Via, Jr. | ..................... 250/516.1 |
| 4,938,233 A | * | 7/1990 | Orrison, Jr. | ................. 128/849 |
| 6,459,091 B1 | * | 10/2002 | DeMeo et al. | ........... 250/516.1 |

\* cited by examiner

*Primary Examiner*—Jurie Yun
(74) *Attorney, Agent, or Firm*—Andrus, Sceales, Starke & Sawall, LLP

(57) ABSTRACT

The invention relates to a device arrangement for intraoral X-ray imaging comprising an X-ray source unit for generating X-radiation and an intraoral sensor placed in the mouth for X-ray imaging, which receives X-radiation for compiling X-ray image data. The device arrangement comprises a protective garment, which garment protects the patient from X-radiation passing the intraoral sensor, and in which protective garment is located an electronics unit for the X-ray image data received by the intraoral sensor. The X-ray image data is transmitted from the intraoral sensor to the electronics unit by means of first data transfer means comprised in the device arrangement, the device arrangement further comprising second data transfer means for transmitting data between the electronics unit located in the protective garment and the rest of the device arrangement.

4 Claims, 5 Drawing Sheets

PROTECTIVE GARMENT

FIELD OF THE INVENTION

The present invention relates to intraoral X-ray imaging, where a sensor placed in the mouth is utilised in the X-ray imaging of human teeth.

BACKGROUND ART

In a solution according to the background art, a sensor is placed in a human mouth for X-ray imaging. This sensor is called an intraoral sensor. In conjunction with the intraoral sensor is located the sensor's electronics unit. An X-ray source is placed in an imaging position outside the mouth, where the X-ray source generates X-radiation at the imaging moment, the purpose of which is to meet the object being imaged and through it the intraoral sensor. The image data comprised in the X-radiation received by the intraoral sensor is usually transmitted via a wired connection from the intraoral sensor to the electronics unit.

However, in practice some of the X-radiation generated by the X-ray source radiates also elsewhere than to the intended area due, for example, to the magnitude of the X-ray cone of rays, diffuse radiation and inadequate positioning of the sensor. The patient is protected from this passing radiation by means of a protective garment placed around the neck, which contains material impenetrable to X-radiation, such as lead. It is important to protect at least the patient's critical organs, such as the thyroid which is located in the neck.

FIGS. 1 and 2, as well as FIG. 3, show a prior art solution, where an electronics unit 108 in wired connection 104 with an intraoral sensor 102 is located separate from the protective garment 113, typically at least at a distance of a few meters from the intraoral sensor and protective garment, for example on a table in the vicinity of a computer. As a result, there is a relatively long wired connection between the intraoral sensor and the electronics unit, which causes, for example, a risk of tripping and of injury to the person tripping over. When tripping over, the electronics unit may fall on the floor and be damaged.

Since the electronics unit is located separate from the protective garment and is unprotected from radiation, another disadvantage is the electronics unit being subjected to diffuse radiation, which may result in an increase in noise deteriorating the quality of the image data and causing premature damage to the electronics unit.

BRIEF SUMMARY OF THE INVENTION

The aim of the invention is to provide an implementation for intraoral X-ray imaging improving practicality and safety. This aim is achieved by means of the device arrangement according to the invention for intraoral X-ray imaging comprising an X-ray source for generating X-radiation and an intraoral sensor placed in the mouth for X-ray imaging, which receives X-radiation for compiling X-ray image data. The device arrangement comprises a protective garment, which garment protects the patient from X-radiation, and in which protective garment is located an electronics unit for the X-ray image data received by the intraoral sensor, which X-ray image data is transmitted from the intraoral sensor to the electronics unit by means of first data transfer means comprised in the device arrangement. The device arrangement further comprises second data transfer means for transmitting data between the electronics unit located in the protective garment and the rest of the device arrangement.

The invention is based on the fact that in the protective garment placed around a patient's neck is located an electronics unit so that the protective garment is no longer merely a garment protecting the patient from radiation, but the functionality of the protective garment is utilised in new ways.

The advantage of the invention is that while the protective garment protects the patient from radiation, it also acts as a storage place for the electronics unit and thus the distance between the intraoral sensor in the mouth and the electronics unit is short. The risk of tripping over the cord between the intraoral sensor and the electronics unit is thus eliminated, as is the risk of the electronics unit falling on the floor.

In the solution according to the invention, the electronics unit no longer hangs loose, but the electronics unit is located through practical positioning in the protective garment, which prevents both the electronics unit and the intraoral sensor from falling on the floor in applications where there is a wired connection between the intraoral sensor and the electronics unit. By means of the implementation according to the invention it is also possible to gain advantage by utilising wireless data transfer technology in data transfer links to other parts of the intraoral device arrangement, thus making possible a more inconspicuous and easily movable implementation of the intraoral device.

LIST OF FIGURES

DETAILED DESCRIPTION OF THE INVENTION

Figure 1:
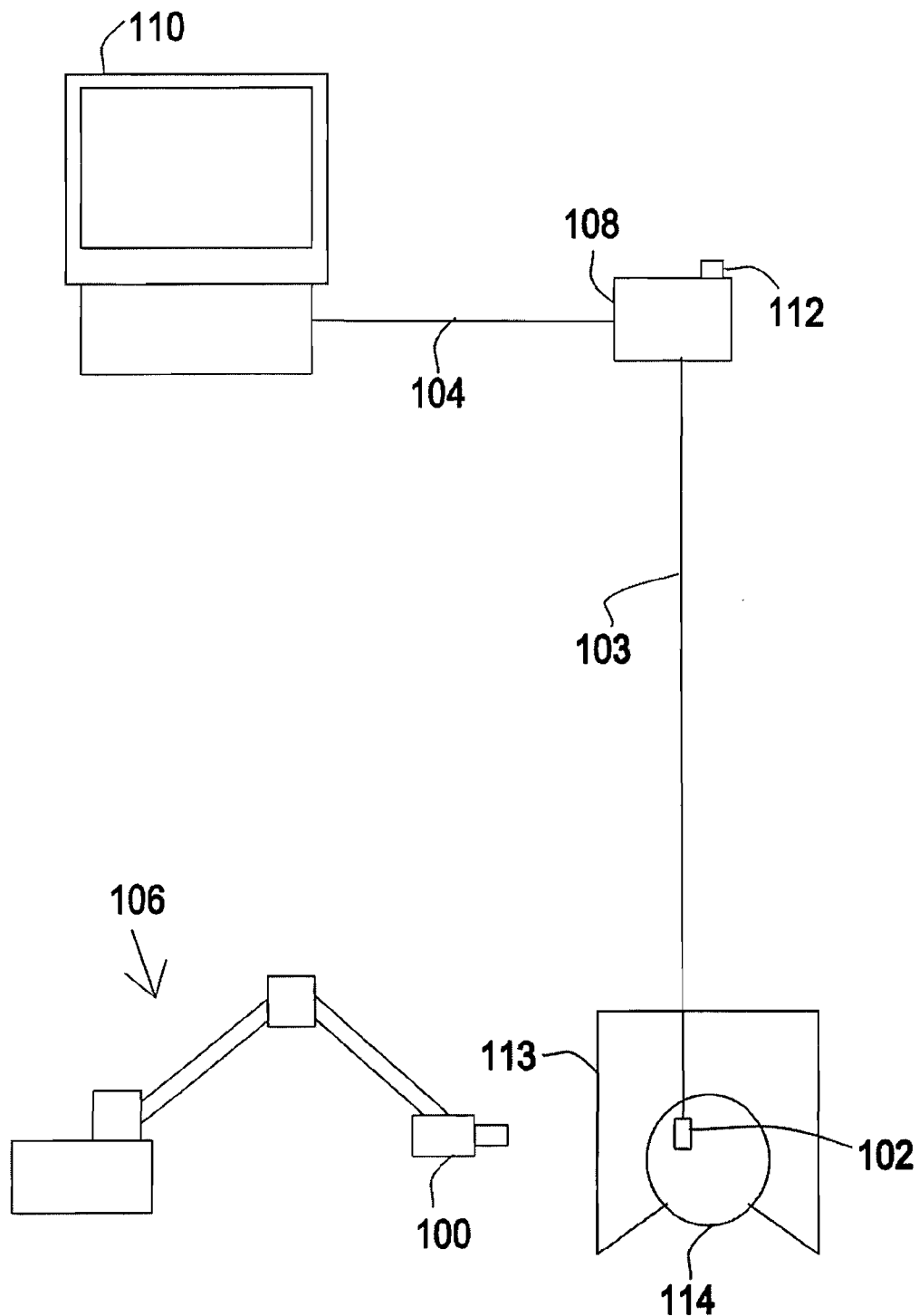
FIG. 1 shows an intraoral imaging apparatus, where wired data transfer links are used.
Figure 2:
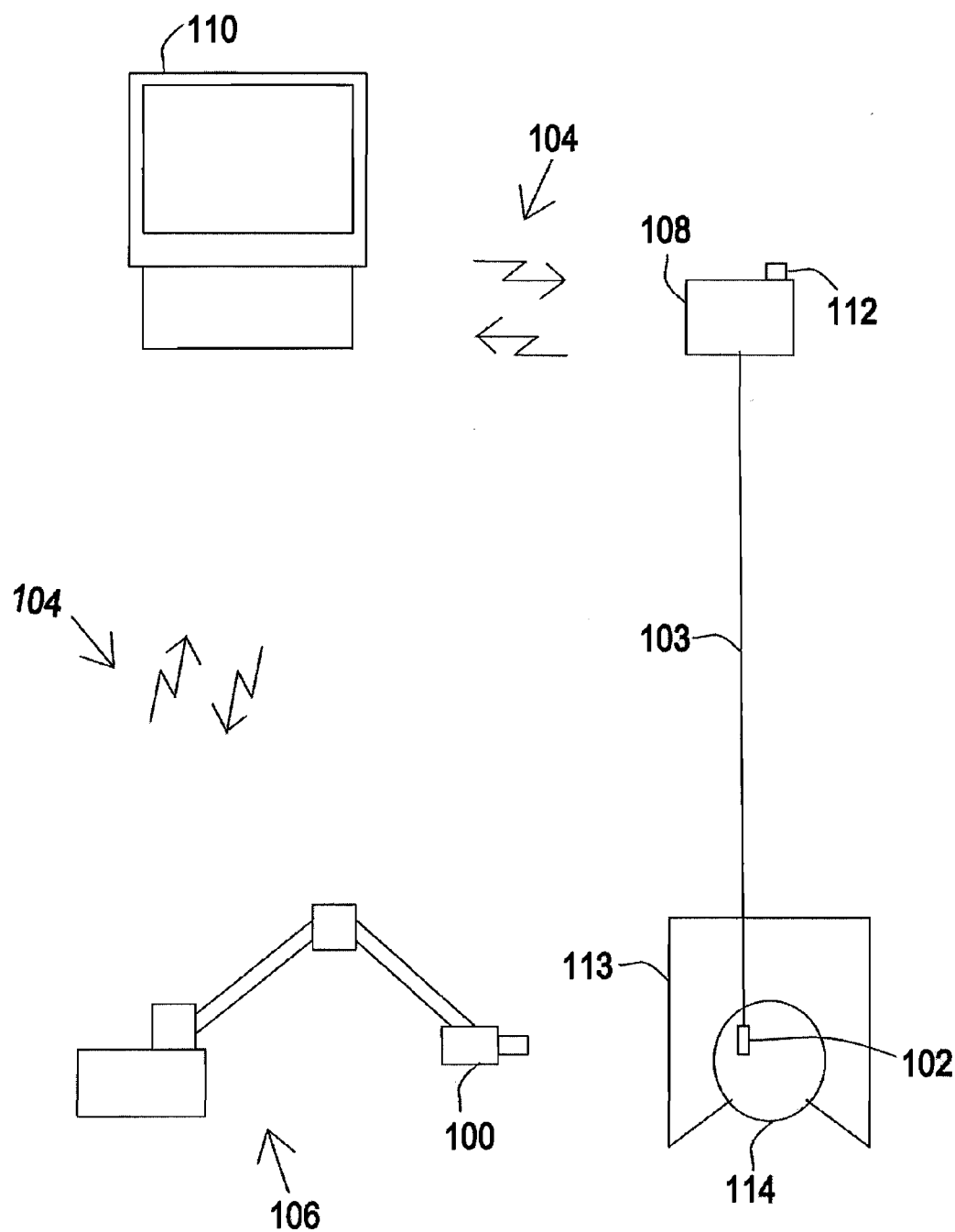
FIG. 2 shows an intraoral imaging apparatus, where wireless data transfer links are used.
Figure 3:
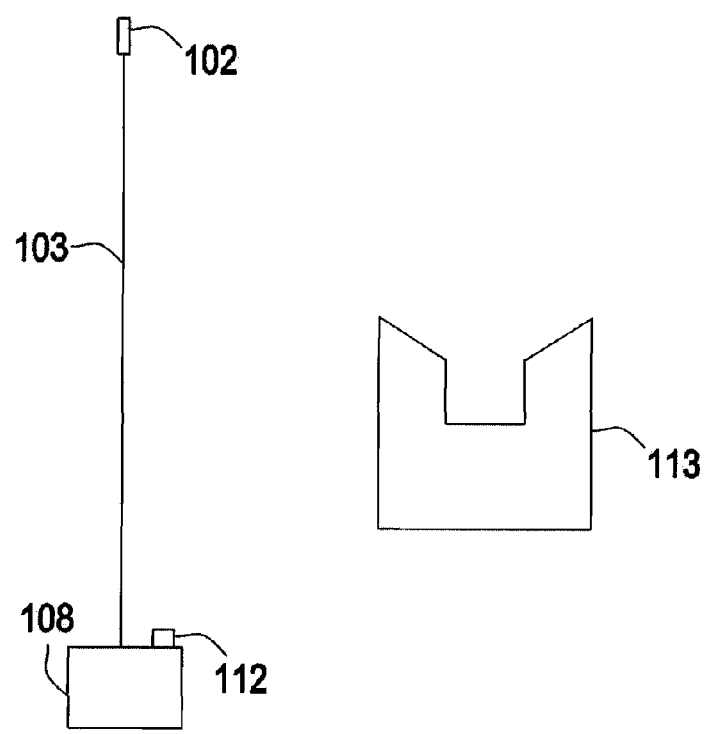
FIG. 3 shows a prior art solution, where the electronics unit is located separate from the protective garment.

In the following, the intraoral imaging apparatuses shown in connection with FIGS. 1 and 2 are otherwise similar, but in FIG. 1 are used wired data transfer links 104, whereas in FIG. 2 some of the data transfer links are realised wirelessly. The intraoral imaging apparatuses shown in FIGS. 1 and 2 comprise an X-ray source unit 100 for producing X-radiation and an intraoral sensor 102 placed in the mouth of the patient for receiving the X-radiation passing through the object. The X-ray source unit comprises an X-ray tube and typically also a collimator. The X-ray source unit is preferably located in connection with an articulated arm arrangement 106 through which the X-ray source unit can be moved to different irradiating positions around the patient's mouth. The intraoral sensor is preferably a digital image sensor which is divided into different imaging areas or pixels.

The image data is compiled of the X-radiation that has passed through the object and been received by the intraoral sensor. The X-ray imaging arrangement comprises an electronics unit 108 located, for example, at a distance of 2 m-10 m from the intraoral sensor. Between the intraoral sensor and the electronics unit is a wired link over the distance of 2-10 meters or some other distance. In the electronics unit, the image data in electronic form, formed on the intraoral sensor receiving X-radiation, is processed as required, typically at least by receiving the image data in the electronics unit and modifying it into the desired format, and sending the image data from the electronics unit elsewhere in the intraoral device arrangement. Thus the electronics unit comprises at least the electronics required to perform the said functions. The electronics unit may also comprise electronics required for storing image data. The electronics unit is realised by process electronics or other prior art technique.

From the electronics unit there is either a wired or wireless data transfer link 104 to a computer unit 110. By means of the computer unit are carried out the storing of image data, further processing of image data and/or examination of X-rays for making a diagnosis. There may be one or more computer units. The computer unit may be located in the same room as the rest of the intraoral imaging apparatus or, in this world of modern data communications, the computer unit may be located, for example, on the other side of the world than the rest of the intraoral imaging apparatus.

Figure 4:
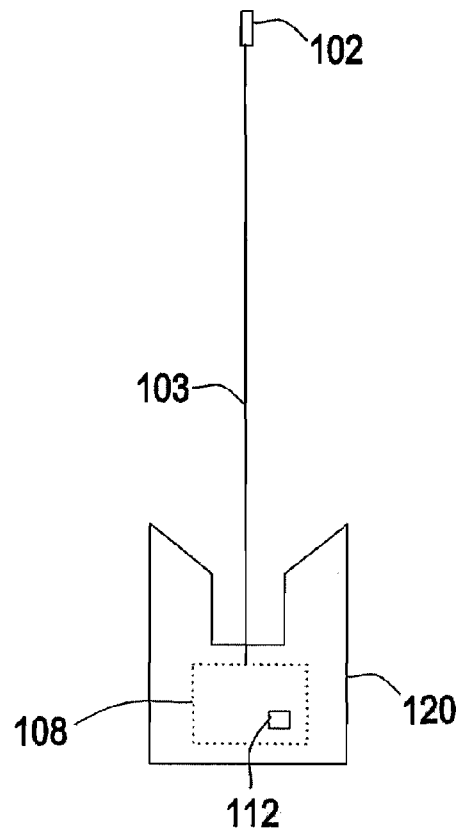
FIG. 4 shows the solution according to the invention, where the electronics unit is located in the protective garment.

FIG. 4 shows a preferred embodiment of the invention, where the electronics unit is located in the protective garment 120 according to the invention. The intraoral sensor 102 is placed in the patient's mouth for the imaging and the protective garment 120 is placed around the patient's neck. A preferred embodiment of the invention may be realised, for example, with intraoral imaging apparatuses such as those shown in FIGS. 5 and 6. In conjunction with the electronics unit located in the protective garment according to the invention may also be arranged a user interface 112, by using which the imaging can be started. The user interface may also comprise other desired forms of use. During imaging, the object being imaged is irradiated by X-radiation generated by the X-ray source 100. The intraoral sensor receives the X-radiation that has passed through the object, which the intraoral sensor converts into image data of the object imaged in electronic form. The image data in electronic form is transmitted via a protected cable 103 to the electronics unit 108 located in the protective garment 120.

From the electronics unit 108 located in the protective garment 120 according to the invention the processed data is transmitted via a transmitter elsewhere in the intraoral imaging apparatus. At this stage, the image data is most typically received by the computer unit 110 on which the image data can be stored and by which computer at least previewing of the image data can be carried out.

Figure 5:
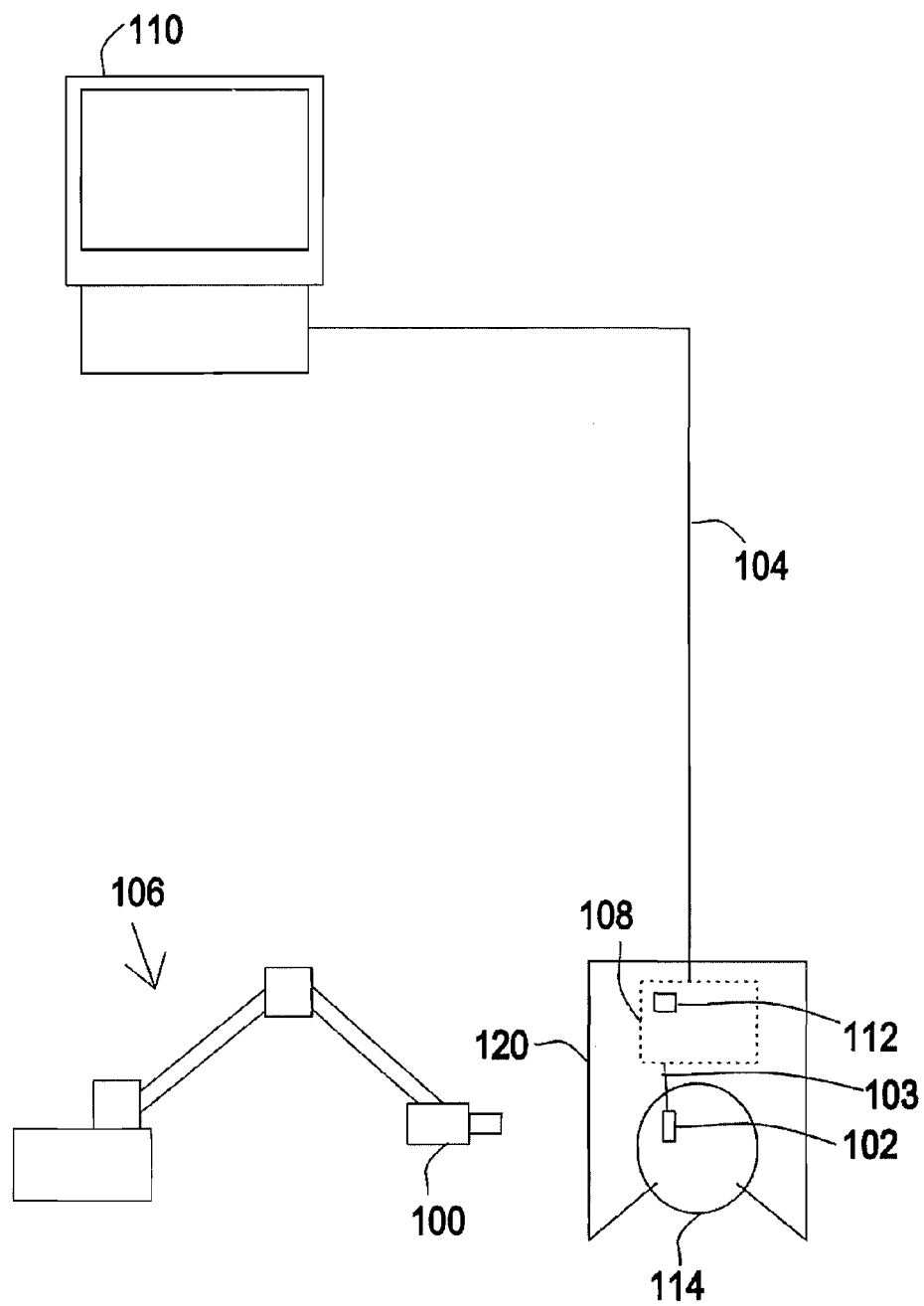
FIG. 5 shows the solution according to the invention in an intraoral imaging apparatus using wired data transfer links.
Figure 6:
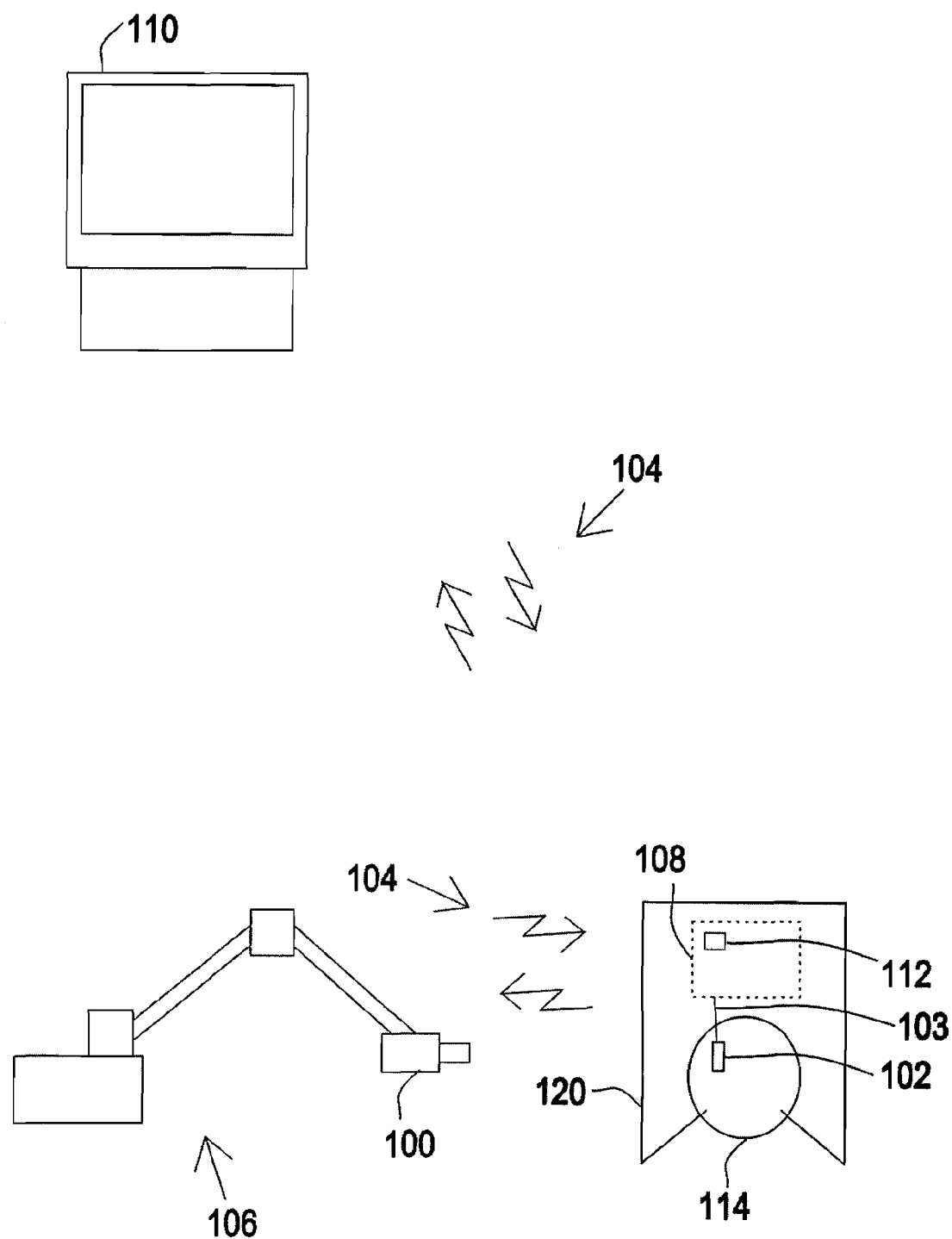
FIG. 6 shows the solution according to the invention in an intraoral imaging apparatus using wireless data transfer links.

FIG. 5 shows the solution according to the invention in an intraoral imaging apparatus using wired data transfer links 104. FIG. 6 shows the solution according to the invention in an intraoral imaging apparatus using wireless data transfer links 104. There may be a data transfer link—either wired or wireless—from the electronics unit also to the X-ray source 100. Along the data transfer link may be communicated, for example, information relating to Automatic Exposure Control (AEC) between the X-ray source 100 and the electronics unit 108 and the rest of the intraoral imaging apparatus. In other respects, the intraoral imaging apparatuses of FIGS. 5 and 6 correspond to those described in connection with FIGS. 1 and 2.

In size and shape the protective garment according to the invention may be as desired provided that the minimum requirements on protectiveness are met. For example in some countries, there can be legislative regulations on the compulsory use of a protective garment. The protective garment may be a collar-type protective garment mainly protecting the neck and the area around the neck, or the protective garment may also be considerably larger. In addition to the electronics unit 108 and the user interface 112, the protective garment 120 according to the invention may also comprise other properties such as a keyboard on which a dentist can type details of the imaging, such as the area in which the X-ray is to be taken. Other details to be typed in could be the key parameters of imaging, such as irradiation time and/or the tube voltage used. The said typed-in details are transmitted by means of the transmitter comprised in the electronics unit, via a data transfer link 104 to the computer unit 110, and through there possibly to a more widespread network.

Technically more detailed implementations than the above have not been described because it is possible to carry them out through device technology, electronically and through programming with prior art implementations.

The invention claimed is:

1. A device arrangement for intraoral X-ray imaging comprising an X-ray source unit for generating X-radiation and an intraoral sensor placed in the mouth for X-ray imaging, which receives X-radiation for compiling X-ray image data, characterised in that the device arrangement comprises a protective garment, which garment protects the patient from X-radiation, and in which protective garment is located an electronics unit for the X-ray image data received by the intraoral sensor, which X-ray image data is transmitted from the intraoral sensor to the electronics unit located in the protective garment by means of first data transfer means comprised in the device arrangement, and which device arrangement further comprises second data transfer means for transmitting data between the electronics unit located in the protective garment and the rest of the device arrangement.

2. A device arrangement as claimed in claim 1, characterised in that as second data transfer means, the device arrangement comprises a transmitter in conjunction with the electronics unit located in the protective garment, which transmitter sends the X-ray image data from the electronics unit along a wireless link and which X-ray image data is received by a receiver located elsewhere in the device arrangement.

3. A device arrangement as claimed in claim 1, characterised in that as second data transfer means, the device arrangement comprises a transmitter in conjunction with the electronics unit located in the protective garment, which transmitter sends the X-ray image data from the electronics unit along a wired link elsewhere in the device arrangement.

4. A device arrangement as claimed in claim 1, characterised in that the device arrangement comprises as protective garment a collar-type protective garment protecting mainly the neck and the area around the neck from X-radiation.

* * * * *